US006755835B2

(12) United States Patent
Schultheiss et al.

(10) Patent No.: US 6,755,835 B2
(45) Date of Patent: Jun. 29, 2004

(54) BONE SCREW

(75) Inventors: Markus Schultheiss, Nersingen (DE); Lutz Claes, Neu-Ulm (DE); Lothar Kinzl, Ulm (DE)

(73) Assignee: Aesculap AG & Co. KG, Tuttlingen (DE)

( * ) Notice: Subject to any disclaimer, the term of this patent is extended or adjusted under 35 U.S.C. 154(b) by 24 days.

(21) Appl. No.: 10/056,989

(22) Filed: Jan. 24, 2002

(65) Prior Publication Data

US 2002/0123752 A1 Sep. 5, 2002

Related U.S. Application Data

(63) Continuation of application No. PCT/EP99/05973, filed on Aug. 14, 1999.

(51) Int. Cl.[7] .......................... A61B 17/56; A61B 17/58; A61F 2/30; A61F 5/00
(52) U.S. Cl. ............................................ 606/73; 606/86
(58) Field of Search ............................ 606/65, 72, 73, 606/92, 93, 94; 411/82, 82.1, 258, 930, 304, 417, 418

(56) References Cited

U.S. PATENT DOCUMENTS

| | | | | |
|---|---|---|---|---|
| 3,911,781 | A | * 10/1975 | Bappert | ......................... 85/47 |
| 4,537,185 | A | 8/1985 | Stednitz | |
| 4,653,489 | A | 3/1987 | Tronzo | |
| 4,712,957 | A | * 12/1987 | Edwards et al. | ............... 411/82 |
| 5,047,030 | A | * 9/1991 | Draenert | ...................... 606/65 |
| 5,098,435 | A | * 3/1992 | Stednitz et al. | ............... 606/73 |
| 5,340,362 | A | 8/1994 | Carbone | |
| 5,693,099 | A | 12/1997 | Härle | |
| 6,048,343 | A | * 4/2000 | Mathis et al. | .................. 606/72 |
| 6,214,012 | B1 | * 4/2001 | Karpman et al. | .............. 606/93 |
| 6,280,675 | B1 | 8/2001 | Legrand | |

FOREIGN PATENT DOCUMENTS

| | | |
|---|---|---|
| DE | 37 04 089 | 8/1988 |
| DE | 41 22 950 | 1/1993 |
| EP | 0 428 127 | 5/1991 |
| EP | 0 434 604 | 6/1991 |
| EP | 0 516 569 | 12/1992 |
| EP | 0 305 417 | 6/1995 |

OTHER PUBLICATIONS

*Patent Abstracts of Japan*, vol. 1997, No. 10, Oct. 31, 1997; Abstract of Japanese Patent No. 09149906, "Tool for Curing Bone Disease", Publication Date Jun. 10, 1997.

M. Schultheiss et al., "Enhancement of Vertebral Screw Fixation in Osteoporotic Bone by a Special Hollow Screw Dowel", *North Sea Biomaterials*, Clinical Conference on Orthopaedics, The Hague, The Netherlands, 1998.

* cited by examiner

*Primary Examiner*—Eduardo C. Robert
*Assistant Examiner*—Anuradha Ramana
(74) *Attorney, Agent, or Firm*—Barry R. Lipsitz; Douglas M. McAllister

(57) ABSTRACT

In order to produce a bone screw having a screw body which is provided with an external thread and which comprises a flow-through mechanism for bone cement that is used for the production of a cement jacket around the bone screw, such that the bone screw will be anchored in a highly stable manner after being implanted in a bone and especially after being implanted in a bone of reduced quality, it is proposed that the flow-through mechanism should comprise at least one longitudinal recess which is formed in the screw body such that it extends transversely relative to the radial direction and/or transversely relative to the peripheral direction.

59 Claims, 4 Drawing Sheets

BONE SCREW

The present invention relates to the subject matter disclosed in international application PCT/EP 99/05973 of Aug. 14, 1999, the entire specification of which is incorporated herein by reference.

BACKGROUND OF THE INVENTION

The invention relates to a bone screw having a screw body which is provided with an external thread and which comprises flow-through means for bone cement that is used for the production of a cement jacket around the bone screw.

Bone screws of this type are, for example, employed as anchoring screws in a stabilisation system when several bone elements have to be connected together. The formation of a cement jacket around the bone screw following the implantation process increases the stability of the anchorage. This is of particular importance when the bone is of reduced quality, such as is the case for osteoporosis of the bony tissue for example.

A bone screw comprising a longitudinal channel along which there is provided a plurality of radially extending transverse channels that are in contact with this longitudinal channel is known from EP 0 305 417 B1.

Based upon this prior art, the object of the invention is to provide a bone screw which, in comparison with the bone screws known from the prior art, will be anchored in a highly stable manner after being implanted in a bone, and especially after it has been implanted in bones of reduced quality.

SUMMARY OF THE INVENTION

In accordance with the invention, this object is achieved in the case of a bone screw of the type mentioned hereinabove, in that the flow-through means comprises at least one longitudinal recess which is formed in the screw body such that it extends transversely relative to the radial direction and transversely relative to the peripheral direction.

By virtue of a recess which is constructed and arranged in this manner and by means of which bone cement can be introduced into the intermediary space between an implanted bone screw and the bone bed, a uniform cement jacket can be formed around the screw. As a result of this feature, the bone screw in accordance with the invention will be anchored in a highly stable manner. Each of the areas between the turns of the external thread can be supplied with bone cement and a highly effective flow of bone cement can be achieved by means of such a longitudinal recess which is formed substantially along the length of the screw body. By contrast, in the case of the bone screw of EP 0 305 417 B1, an individual radial channel basically has to be provided for each of the intermediary spaces. Moreover, in order to also enable a cement jacket to be built-up in the region around the frontal end of the screw, the longitudinal channel used there must extend through the whole of the screw body. Construction of the screw in the form of a self-tapping screw is thereby adversely affected. By contrast, in the case of the bone screw in accordance with the invention, a longitudinal recess basically suffices, and a cement jacket can also be formed about the frontal end of the bone screw by means of appropriate recesses in the turns of the external thread.

It is expedient if the at least one longitudinal recess is arranged such that it is perpendicular to the radial direction and especially so, if it is arranged to be perpendicular to the peripheral direction.

It is particularly advantageous if the flow-through means comprise a hollow channel formed in the screw body and if a longitudinal recess is connected to the hollow channel. Consequently, bone cement introduced into the hollow channel can flow out directly from the body of the screw via such a longitudinal recess without encountering substantial barriers to the flow of material so as to form a uniform cement jacket around the bone screw. It is thereby ensured that the bone screw in accordance with the invention will be anchored in a highly stable manner after the implantation process. It is expedient if a longitudinal recess is connected to the hollow channel in the longitudinal direction of said recess so as to minimise the resistance encountered by the flow of bone cement.

It is particularly advantageous if the dimensions of a longitudinal recess in the longitudinal direction thereof are such that it extends over a plurality of turns of the external thread. Due to this feature, the bone cement can be supplied to the whole of the screw body using essentially just one longitudinal recess.

In a particularly advantageous embodiment, a longitudinal recess has corresponding recesses associated therewith in the turns of the external thread. This enables the bone cement to flow between different intermediate regions i.e. the regions between adjacent turns of the thread so as to enable the bone cement to be distributed uniformly and thus produce a uniform build-up of the cement around an implanted bone screw. It is expedient if a turn of the external thread is broken-through in the vicinity of a longitudinal recess so as to enable the bone cement to flow therethrough.

For manufacturing purposes, it is particularly expedient if a longitudinal recess is in the form of a slot. This feature enables the recess to be produced in a simple manner by a machining process, for example, a milling process. It is advantageous if a plane of the slot is substantially perpendicular to the peripheral direction of the screw body. In particular hereby, the slot is formed by an upper slot plane and a lower slot plane which are in parallel with one another. Due to the construction perpendicular to the peripheral direction, the slot plane can be oriented in the radial direction. This enables an efficient flow of bone cement when the screw body is rotationally symmetrical. Furthermore, it is also expedient if a plane of the slot is disposed substantially radially relative to the screw body.

It is particularly advantageous if a plane of the slot is located substantially longitudinally relative to the screw body. On the one hand, this ensures that such a longitudinal recess is easy to produce, and it also ensures an efficient flow of bone cement on the other.

For the purposes of forming a cement jacket which will ensure a high degree of stability for the anchorage, it is particularly advantageous if a plurality of longitudinal recesses are arranged over the periphery of the screw body. This feature ensures that the regions between the turns of the external thread taken with reference to the periphery of the screw body will be uniformly supplied with bone cement.

In one advantageous variant of this embodiment, three longitudinal recesses are arranged along the periphery of the screw body. On the one hand, this enables the number of break-throughs in the turns of the external thread and in the body of the screw to be kept low, and it also enables uniform application of the bone cement on the other.

Hereby, it is of especially great advantage if the plurality of longitudinal recesses are substantially symmetrical relative to a longitudinal axis of the screw body. In this manner, the bone cement, which is introduced into the body of the screw, flows uniformly via the longitudinal recesses into the regions between the turns of the external thread and forms a uniform cement jacket.

In a particularly advantageous embodiment, the bone screw in accordance with the invention comprises successive sections in the longitudinal direction of the screw body which differ in regard to the construction of the outer surfaces thereof. Due to these outer surfaces being constructed such as to have differing geometrical shapes, a particularly highly stable anchorage is attainable by, on the one hand, forming one or more sections which will ensure that the thread is held firmly in the bone and, on the other hand, forming sections which will exhibit a sealing effect in regard to the outward flow of the bone cement. In this manner, a cement jacket can be built-up which will increase the anchoring forces in every direction by virtue of it interlocking with the bone in the manner of meshing gears. The volume of bone cement that needs to be supplied can be precisely metered by appropriate selection of the dimensions of the sections. Consequently, problems associated with the heating effects produced by reactions in the cement are, to a great extent, avoided.

It is expedient if a frontal section of the screw body is substantially conical or is in the form of a truncated cone. An effective self-tapping function of the thread is thereby obtained. On the other hand, such a section is effective as a seal for preventing unintentional outflow of the bone cement.

Hereby, it is expedient if the envelope of the turns of the external thread is substantially conical or is in the form of a truncated cone in the frontal section thereof so as to obtain an effective self-tapping function for the thread. It is expedient if the envelope of the screw body is substantially conical or is in the form of a truncated cone in the frontal section thereof so as to produce a sealing effect for preventing unintentional outflow of the bone cement.

Furthermore, it is advantageous if a central section of the screw body is substantially cylindrical. The thread of an implanted screw will be held firmly in the bone by virtue of such a cylindrical section. Hereby, it is expedient if the envelope of the turns of the external thread in the central section is substantially cylindrical, and likewise, if the envelope of the screw body in the central section is substantially cylindrical.

It is of particularly great advantage if a hollow channel in the screw body is led through the central section, and especially if it is extended up to or close to the frontal section. The hollow channel does not then need to be continuous so that the self-tapping effect at the frontal end of the thread will not be adversely affected although, on the other hand, the bone screw can nevertheless still be uniformly coated with bone cement so as to form a cement jacket. For the same reasons, it is advantageous if the at least one longitudinal recess is arranged substantially in the central section.

It is expedient if a rear section of the screw body is substantially conical or is in the form of a truncated cone. By virtue of such a conical end region of the bone screw in accordance with the invention, a sealing effect for preventing unintentional outflow of bone cement from the bone bed in the case of an implanted bone screw can again be achieved.

Hereby, it is of particularly great advantage if the envelope of the screw body is substantially conical or is in the form of a truncated cone in the rear section so as to obtain the aforesaid sealing effect and if the envelope of the turns of the external thread is substantially cylindrical in the central section. Firstly hereby, one can achieve the sealing effect and secondly, the effect upon the bone caused by the boring action of the screw will not be increased thereby. It is expedient hereby if the envelope of the turns in the rear section and that of the turns in the central section coincide.

For production reasons, it is advantageous if the angle of the cone in the frontal section substantially corresponds to the angle of the cone in the rear section.

In order to form a uniform cement jacket around the bone screw and, in particular, to anchor the bone screw in accordance with the invention with great stability even in the case of bony tissue affected by osteoporosis, provision is made for the turns of the external thread to be provided with longitudinal breakthroughs in a region in which there are no longitudinal recesses. By virtue of this feature, substantially all of the regions surrounding the screw body can be supplied with bone cement since the bone cement is able to flow out from those intermediary spaces which are supplied via the longitudinal recesses and through the longitudinal breakthroughs into those regions that cannot be directly supplied. Thus, for example, a cement jacket can thereby be formed even round the frontal section of the bone screw in accordance with the invention.

It is quite particularly expedient and particularly easy for manufacturing purposes if a surface of the screw body between adjacent turns of the external thread is substantially parallel to the longitudinal direction of the screw body. A larger intermediary space is therefore made available for the bone cement, this thereby enabling, in particular, an effective flow of bone cement into the regions between the individual turns of the external thread for the purposes of distributing the cement around the periphery of the screw body.

For production purposes, it is particularly simple if the hollow channel is in the form of a blind bore.

A multiplicity of ways of utilising the screw are provided if the screw body is provided with an internal thread. In particular thereby, a screw head that may be adapted for a particular application can then be utilised, for example, a spherical head for a polyaxial tension mechanism. It is expedient hereby, if such a screw head is provided with a channel which is connectable to the hollow channel in the screw body so as to enable the bone cement to be supplied to the hollow channel in this manner.

It is of particularly great advantage if the screw body comprises a coupling element for a bone cement applicator. Such a coupling element may, for example, be arranged in a screw head which is formed in one-piece with the screw body or is connected thereto, or, it may be arranged directly in the screw body. It is advantageous if the coupling element comprises a seating arrangement for a nozzle of a bone cement applicator so as to enable bone cement to be injected into the screw body in a simple manner.

An especially stable arrangement for the anchorage is obtained if a diameter of the screw body is greater than a pitch of the external thread. Furthermore, a highly stable anchorage will be obtained if a bone screw in accordance with the invention comprises approximately seven to twelve peripheral turns of the external thread.

It is advantageous if the external thread is constructed in such a manner that the bone screw is self-tapping so as to enable universal usage thereof in this manner.

The following description of preferred embodiments of the invention will serve for a more detailed explanation thereof in conjunction with the drawing.

DETAILED DESCRIPTION OF THE INVENTION

Figure 1:
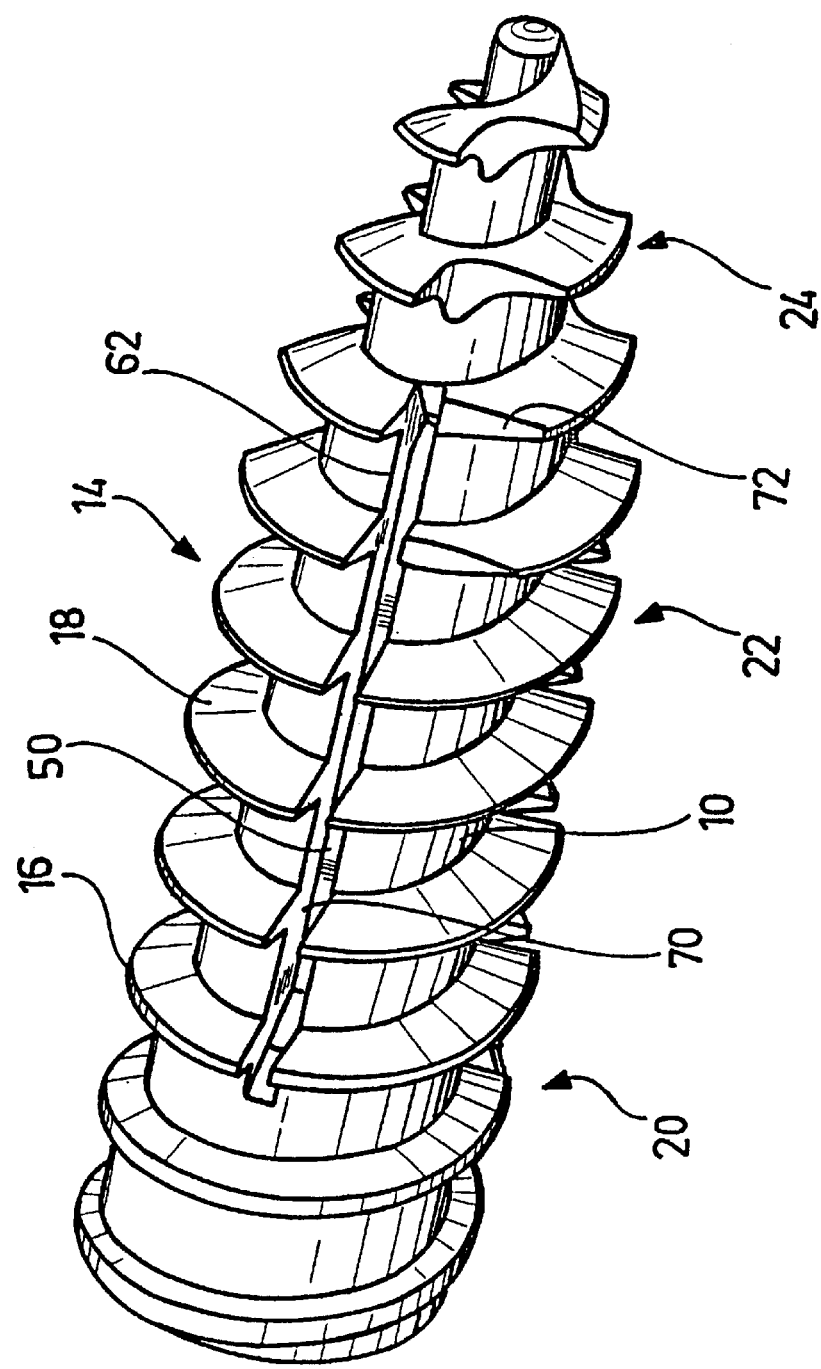
FIG. 1 shows a perspective view of an embodiment of a bone screw in accordance with the invention.
Figure 2:
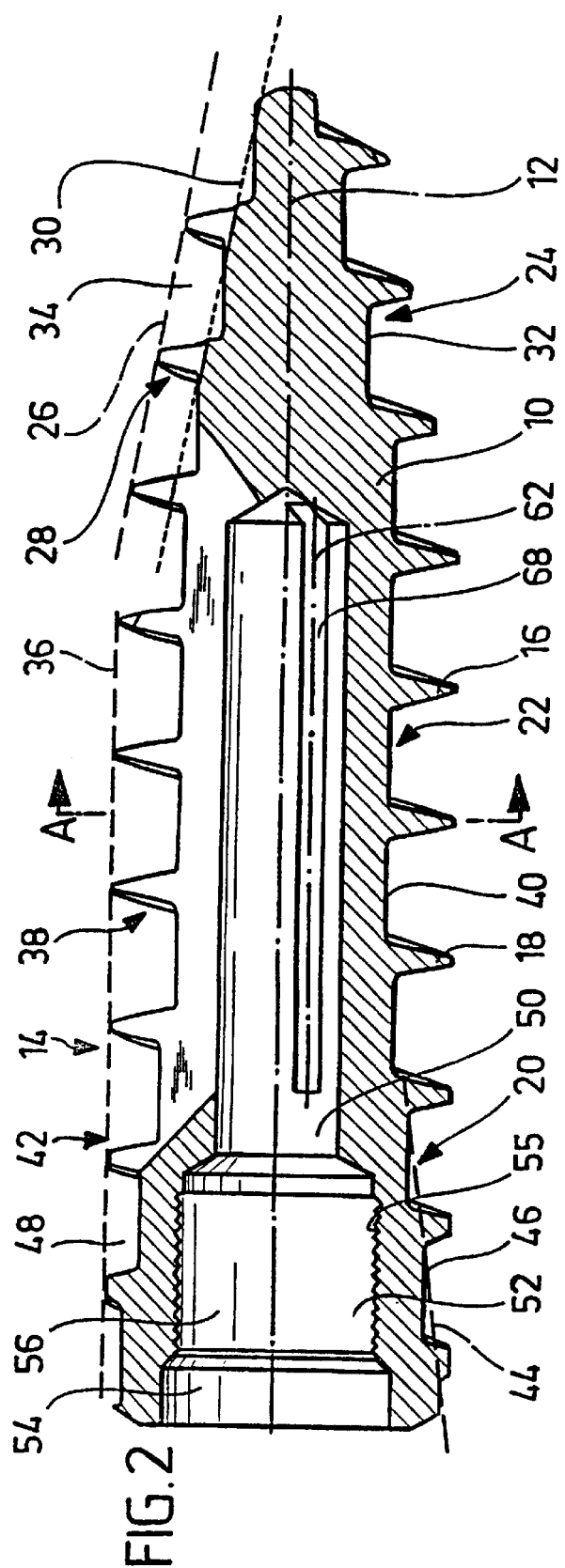
FIG. 2 a lateral sectional view of the bone screw of FIG. 1.

A bone screw in accordance with the invention comprises, as is shown in FIGS. 1 and 2, a screw body 10 which is substantially rotationally symmetrical relative to a longitudinal axis 12. The screw body is provided with an external thread bearing the general reference 14. This thread 14 comprises a plurality of turns 16 of which the flanks 18 thereof are constructed and arranged, in particular, such that the bone screw in accordance with the invention will be self tapping. The external thread 14 is formed in one-piece with the screw body 10. The preferred material for the bone screw is titanium for example.

The bone screw in accordance with the invention comprises successive sections 20, 22, 24 in the longitudinal direction of the screw body 10, said sections differing from one another as regards the outer shape thereof. Hereby, the frontal section 24, which forms the distal end of the bone screw, is in the form of a cone. The envelope 26 of the turns 28 of the external thread 14 in this frontal section 24 is conical and the cone angle thereof lies, for example, in a range of between 5° and 15° and, in particular, the cone angle may be approximately 10°. This envelope 26 is rotationally symmetrical relative to the longitudinal axis 12 of the screw body 10. Moreover, the screw body 10 has an envelope 30 in the frontal section 24 thereof, this envelope likewise being conical and extending co-axially relative to the envelope 26, i.e. it has substantially the same cone angle as that of the envelope 26. One obtains the envelope 30 by virtue of the intersection formed between the flanks 18 of the turns 28 and the screw body 10 in the frontal section 24 as is depicted in FIG. 2. In the frontal section 24 itself, the outer surface 32 of the screw body 10 that is formed between the turns 28 is cylindrical, i.e. it is parallel to the longitudinal axis 12 and, as a result thereof, it is not inclined relative thereto and thereby provides a larger intermediary space 34 between adjacent turns 28.

A central section 22 having a cylindrical envelope 36 adjoins the frontal section 24 in the proximal direction; consequently, the turns 38 in the central section 22 are of the same height. The outer surface 40 of the screw body 10 in the central region 22 is likewise cylindrical and co-axial relative to the envelope 36.

A rear section 20 adjoins the central section 22 in the proximal direction, the turns 42 in the rear section having the same envelope as the turns 38 in the central section 22, i.e. the turns 42 have a cylindrical envelope. The envelope 44 of the screw body 10, which is defined by the intersection of the turns 42 with the screw body 10 in the rear section 20, is in the form of a cone having a cone angle which is approximately 10° for example. Hereby, the outer surface 46 of the screw body 10 in the rear section 20 has a cylindrical shape between adjacent turns 42 so as to produce larger intermediary spaces 48 for the bone cement between the adjacent turns 42 in the rear section 20 in a similar manner to that provided in the frontal section 24. Consequently, the turns 42 above the screw body 10 have differing heights relative to the screw body 10 in the rear section 20.

Figure 4:
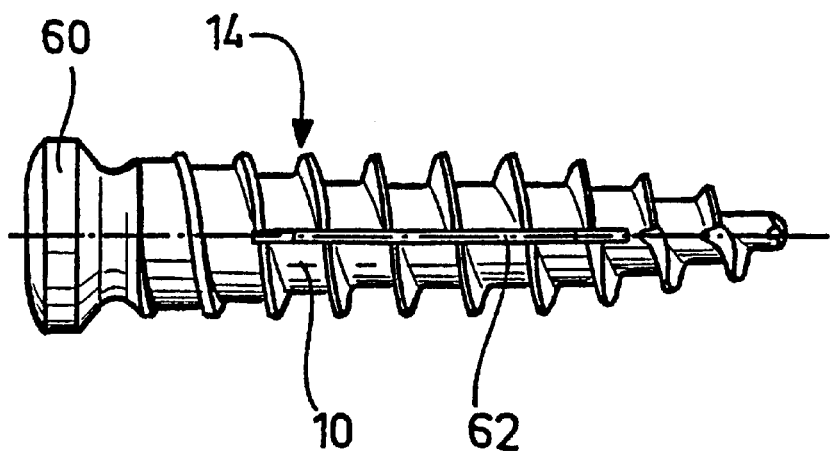
FIG. 4 a side view of a further embodiment of a bone screw in accordance with the invention.
Figure 5:
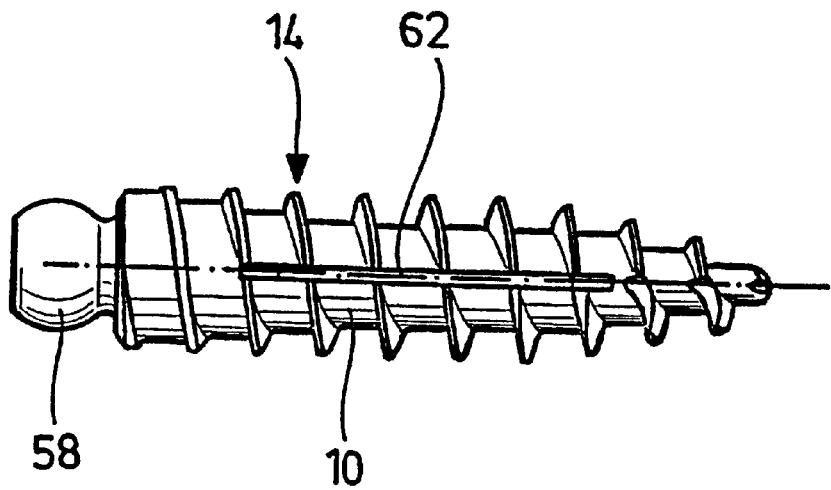
FIG. 5 a side view of the embodiment of FIG. 1 having a screw head set in place and FIG. 6 a schematic illustration of a bone cement applicator for applying bone cement which is attached to the screw shown in FIG. 5.
Figure 6:
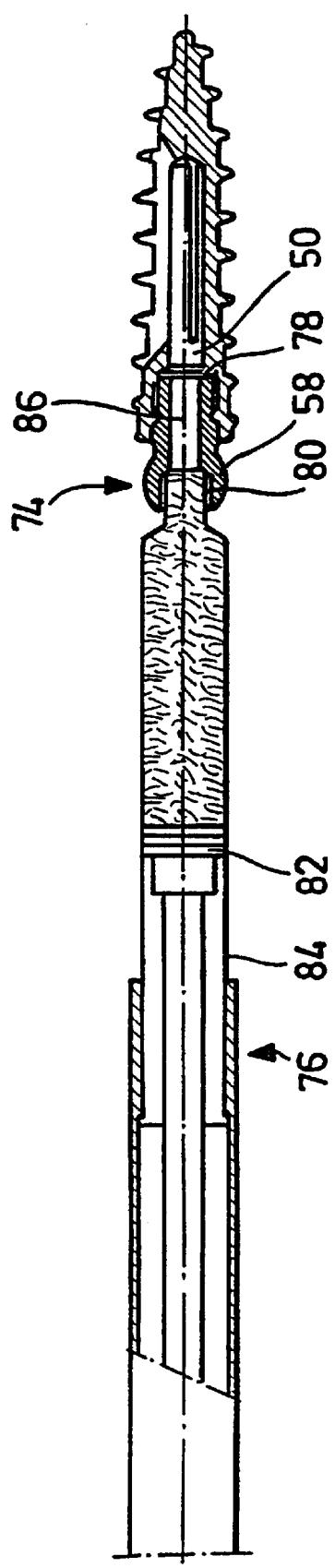

The bone screw comprises flow-through means with the aid of which bone cement can be introduced through the screw body 10 into the intermediary spaces 34, 48 and especially into the spaces between the turns 38 in the central section 22. To this end, there is provided in the screw body 10, a hollow channel 50 which is coaxial relative to the longitudinal axis 12 and, for example, is in the form of a blind bore which extends through the rear section 20 and the central section 22 into the transition region between the central section 22 and the frontal section 24. In the case of the embodiment shown in FIG. 2, the screw body 10 comprises a recess 52 in the rear section 20 thereof, and the hollow channel 50 is adjoined to this said recess. The recess 52 comprises a first cylindrical region 54 and a second cylindrical region 56, the first cylindrical region 54 having a greater diameter than that of the second cylindrical region 56. The recess 52 is provided with an internal thread 55. A screw head 58 can be inserted into the internal thread 55 in this recess 52 as is depicted in FIGS. 5 and 6, said head being constructed in accord with the application of use. It is also possible to form the screw head 60 in one-piece with the bone screw as is shown in FIG. 4.

Figure 3:
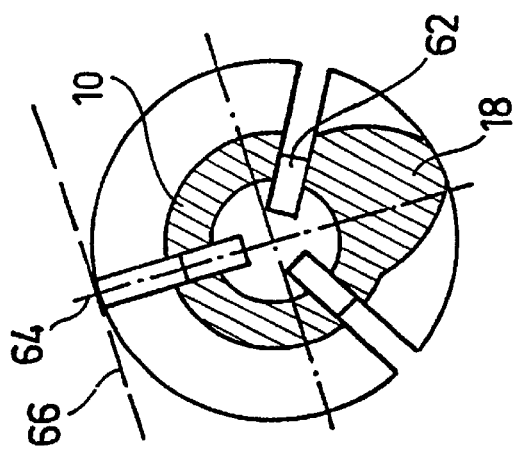
FIG. 3 a sectional view along the line A—A of FIG. 2.

The flow-through means for the bone cement in the screw body 10 is in the form of at least one longitudinal recess 62 which is transverse and, more particularly, perpendicular to the radial direction 64, and it is also transverse to and, more particularly, perpendicular to the peripheral direction 66 (FIG. 3). The bone cement can flow via the hollow channel 50 into the intermediary spaces between the turns 16 with the aid of such longitudinal recesses 62. A longitudinal recess 62 comprises a longitudinal axis 68 which is preferably parallel to the longitudinal axis 12 of the screw body 10. The dimensions of the longitudinal recess 62 are selected such that the length of the longitudinal recess 62 in a direction along the longitudinal axis 68 thereof is substantially greater than the width transverse thereto, said longitudinal recess 62 extending over a plurality of turns 16 in the central section 22. In the embodiment depicted in FIG. 2, a longitudinal recess extends over the turns 38 in the central section 22 up to the rear section 20.

A longitudinal recess 62 is of slot-like construction (FIG. 3) having a slot plane in the longitudinal direction 12 and the radial direction 64. The slot plane also extends over the turns 16, i.e. they are formed in the turns 16 in the case of the longitudinal recesses 62 and the break-through recesses 70 associated therewith (FIG. 1), the intermediary spaces between adjacent turns 16 corresponding with one another through the recesses 70. The turns 28 in the frontal section 24 of the bone screw and especially those turns through which a longitudinal recess 62 no longer extends, comprise larger breakthroughs 72. In this manner, bone cement can flow into those intermediary spaces 34 which are not themselves directly connected to the hollow channel 50 (but are only indirectly connected thereto via the break-throughs 72).

As is depicted in FIG. 3, a bone screw preferably comprises a plurality of longitudinal recesses 62, three such longitudinal recesses for example, which are arranged around the periphery of the screw body 10. In particular, the longitudinal recesses 62 are arranged symmetrically about the longitudinal axis 12 so as to enable the intermediary spaces between the turns to be filled with bone cement in a uniform manner.

In a variant of the embodiment which is depicted in FIG. 6, a coupling element 74 for a bone cement applicator 76 is disposed at the rear end of the hollow channel 50. In the embodiment shown, the coupling element 74 is formed in the inserted screw head 58. The coupling element 74 comprises a preferably annular seating surface 78 for a nozzle 80 of the bone cement applicator 76.

The bone cement applicator 76 comprises an actuating element (not shown in FIG. 6) by means of which an operator controls the supply of bone cement to a bone screw in accordance with the invention. A plunger 82 can be displaced longitudinally by means of the actuating element. A replaceable bone cement cartouche 84 can be inserted into the bone cement applicator 76 and the bone cement can be introduced into the hollow channel 50 by the nozzle 80 from the cartouche 84 by means of the plunger 82. To this end, the screw head 58 comprises a channel 86 which is connected to the hollow channel 50.

Exemplary dimensions for a bone screw in accordance with the invention are a length of 40 mm, a diameter of the screw thread 10 of 6 mm (in the central section 22), a diameter of 10 mm for the external thread 14 (in the rear section 20 and in the central section 22) and a thread pitch of 4 mm for the external thread. Preference is given to having three longitudinal recesses 60 around the periphery of the screw body 10.

The bone screw in accordance with the invention may now be employed as follows:

The bone screw in accordance with the invention can, for example, be used as an anchoring screw in a stabilising system that is utilised when connecting bone elements. The bone screw is implanted into a bone by means of the self-tapping thread; this is effected, in particular, by screwing it in by means of the self-tapping external thread 14. In order to increase the stability of the anchorage, bone cement is introduced into the intermediary space between the bone bed and the bone screw inserted into the bone bed so as to build-up a cement jacket around the bone screw. To this end for example, the bone cement, which must have a suitably low viscosity, is injected through the screw head 58 by means of the bone cement applicator 76 and the cement then flows via the hollow channel 50 through the longitudinal recesses 62 into the intermediary spaces between the turns 16. The bone cement can flow into the intermediary spaces 34 in the frontal section 24 of the bone screw via the break-throughs 72. A cement jacket, which surrounds the bone screw, is thereby formed between the bone screw and the bone bed so that the anchoring forces of the bone screw are increased in every direction by virtue of the interlocking, meshing effect with the bone that is produced by means of the cement jacket. In addition, if the quality of the bone is reduced such as is the case for a bone affected by osteoporosis for example, the bone cement can penetrate further into the bony tissue.

The conical construction of the rear section 20 and the frontal section 24 increases the sealing effect of the bone screw in regard to the flow of bone cement so that an unintentional outflow of bone cement from the bone bed will, to a large extent, be prevented.

Test comparisons have shown that the anchorage of the bone screw in accordance with the invention is extremely stable even in bony tissue affected by osteoporosis. The average attainable strength of the anchorage in a human vertebral body that is affected by osteoporosis and has a bone density of approximately 240 mg/cm$^3$ is, for example, approximately 550 N without the use of bone cement but is approximately 810 N when using bone cement. The anchorage strength achieved in the case of sound tissue is approximately twelve times greater than that for the bone screws known from the prior art.

What is claimed is:

1. A bone screw comprising:
    a screw body which comprises flow-through means for bone cement that is used for the production of a cement jacket around the bone screw, and
    an external thread on said screw body,
    said flow-through means comprising:
        at least one longitudinal recess formed in the screw body extending transversely relative to at least one of a radial direction and a peripheral direction, and said at least one longitudinal recess extending over a plurality of turns of the external thread in a longitudinal direction, and
        a hollow channel extending longitudinally within the screw body from a rear section of said screw body through a central section of said screw body and into at least a portion of a frontal section of said screw body and said at least one longitudinal recess being connected to the hollow channel along at least a portion of said central section of the screw body;
    wherein said bone cement is enabled to flow into said at least one longitudinal recess from said hollow channel and into intermediary spaces between turns of the external thread to produce said cement jacket substantially around said screw body.

2. A bone screw in accordance with claim 1, wherein said at least one longitudinal recess is perpendicular to the radial direction.

3. A bone screw in accordance with claim 1, wherein said at least one longitudinal recess is perpendicular to the peripheral direction.

4. A bone screw in accordance with claim 1, wherein said at least one longitudinal recess is connected to the hollow channel in the longitudinal direction of said recess.

5. A bone screw in accordance with claim 1 wherein said at least one longitudinal recess has corresponding recesses associated therewith in the turns of the external thread.

6. A bone screw in accordance with claim 5, wherein a turn of the external thread is broken-through in the vicinity of said at least one longitudinal recess.

7. A bone screw in accordance with claim 1, wherein said at least one longitudinal recess is in the form of a slot.

8. A bone screw in accordance with claim 7, wherein a plan of the slot is substantially perpendicular to a peripheral direction of the screw body.

9. A bone screw in accordance with claim 7, wherein a plane of the slot is substantially radial taken with respect to the screw body.

10. A bone screw in accordance with claim 7, wherein a plane of the slot lies substantially in the longitudinal direction taken with respect to the screw body.

11. A bone screw in accordance with claim 1 wherein a plurality of longitudinal recesses are arranged over the periphery of the screw body.

12. A bone screw in accordance with claim 11, wherein three longitudinal recesses are arranged over the periphery of the screw body.

13. A bone screw in accordance with claim 11, wherein the plurality of longitudinal recesses are substantially symmetrical relative to a longitudinal axis of the screw body.

14. A bone screw in accordance with claim 1 wherein the rear section, the central section, and the frontal section each differ in regard to the construction of the outer surfaces thereof.

15. A bone screw in accordance with claim 14, herein the frontal section of the screw body is substantially conical or is in the form of a truncated cone.

16. A bone screw in accordance with claim 15, wherein an envelope of the turns of the external thread in the frontal section is substantially conical or is in the form of a truncated cone.

17. A bone screw in accordance with claim 15 wherein an envelope of the screw body in the frontal section is substantially conical or is in the form of a truncated cone.

18. A bone screw in accordance with claim 14 wherein a the central section of the screw body is substantially cylindrical.

19. A bone screw in accordance with claim 18, wherein an envelope of the turns in the central section is substantially cylindrical.

20. A bone screw in accordance with claim 18, wherein an envelope of the screw body in the central section is substantially cylindrical.

21. A bone screw in accordance with claim 14 wherein the hollow channel in the screw body is led through the central section.

22. A bone screw in accordance with claim 14 wherein said at least one longitudinal recess is arranged substantially in the central section.

23. A bone screw in accordance with claim 22, wherein the angle of the cone in the frontal section substantially corresponds to the angle of the cone in the rear section.

24. A bone screw in accordance with claim 14 wherein the rear section of the screw body is substantially conical or is in the form of a truncated cone.

25. A bone screw in accordance with claim 24, wherein an envelope of the screw body in the rear section is substantially conical or is in the form of a truncated cone.

26. A bone screw in accordance with claim 24, wherein an envelope of the turns of the external thread in the rear section is substantially cylindrical.

27. A bone screw in accordance with claim 26, wherein an envelope of the turns in the rear section and of the turns in the central section coincides.

28. A bone screw in accordance with claim 14, wherein the turns of the external thread are provided with longitudinal break-throughs in a region in which there are no longitudinal recesses.

29. A bone screw in accordance with claim 14, wherein a surface of the screw body between adjacent turns of the external thread is substantially parallel to the longitudinal direction of the screw body.

30. A bore screw in accordance with claim 14, wherein a diameter of the screw body is greater than the pitch of external thread.

31. A bone screw in accordance with claim 1, wherein a surface of the screw body between adjacent turns of the external thread is substantially parallel to the longitudinal direction of the screw body.

32. A bone screw in accordance with claim 1 wherein the hollow channel is in the form of a blind bore.

33. A bone screw in accordance with claim 1, wherein the screw body is provided with an internal thread.

34. A bone screw in accordance with claim 1, wherein a screw head for insertion in the screw body is provided with a channel.

35. A bone screw in accordance with claim 1, wherein the screw body comprises a coupling element for a bone cement applicator.

36. A bone screw in accordance with claim 35, wherein the coupling element comprises a seating arrangement for a nozzle of a bone cement applicator.

37. A bone screw in accordance with claim 1, wherein a diameter of the screw body is greater than a pitch of the external thread.

38. A bone screw in accordance with claim 1, wherein a bone screw comprises approximately seven to twelve peripheral turns of the external thread.

39. A bone screw in accordance with claim 1, wherein the external thread is constructed in such a manner that the bone screw is self-tapping.

40. A method for stabilising bone elements using a bone screw, said method comprising:
   screwing said bone screw into adjacent bone elements by means of an external thread provided on a screw body of said bone screw;
   injecting bone cement into a hollow channel extending longitudinally within the screw body from a rear section of said screw body through a central section of said screw body and into at least a portion of a frontal section of said screw body;
   said bone cement flowing through said hollow channel and into at least one longitudinal recess formed on the periphery of the screw body which is connected to the hollow channel along at least a portion of a length of said hollow channel, said at least one longitudinal recess extending transversely relative to at least one of a radial direction and a peripheral direction, and said at least one longitudinal recess extending over a plurality of turns of the external thread in a longitudinal direction;
   said bone cement flowing from said at least one longitudinal recess into intermediary spaces between said turns of the external thread to produce a cement jacket substantially around said screw body.

41. A method in accordance with claim 40 wherein said at least one longitudinal recess has corresponding recesses associated therewith in the turns of the external thread.

42. A method in accordance with claim 41, wherein a turn of the external thread is broken-through in the vicinity of said at least one longitudinal recess.

43. A method in accordance with claim 40, wherein three longitudinal recesses are arranged over the periphery of the screw body.

44. A method in accordance with claim 40, wherein the rear section, the central section, and the frontal section each differ in regard to the construction of the outer surfaces thereof.

45. A method in accordance with claim 44, wherein the frontal section of the screw body is substantially conical or is in the form of a truncated cone.

46. A method in accordance with claim 45, wherein an envelope of the turns of the external thread in the frontal section is substantially conical or is in the form of a truncated cone.

47. A method in accordance with claim 45 wherein an envelope of the screw body in the frontal section is substantially conical or is in the form of a truncated cone.

48. A method in accordance with claim 44 wherein the central section of the screw body is substantially cylindrical.

49. A method in accordance with claim 48, wherein an envelope of the turns in the central section is substantially cylindrical.

50. A method in accordance with claim 48, wherein an envelope of the screw body in the central section is substantially cylindrical.

51. A method in accordance with claim 44 wherein said at least one longitudinal recess is arranged substantially in the central section.

52. A method in accordance with claim 44, wherein the turns of the external thread are provided with longitudinal break-throughs in a region in which there are no longitudinal recesses.

53. A method in accordance with claim 40, wherein the screw body is provided with an internal thread.

54. A method in accordance with claim 40, wherein a screw head for insertion in the screw body is provided with a channel.

55. A method in accordance with claim 40, wherein the screw body comprises a coupling element for a bone cement applicator.

56. A method in accordance with claim 55, wherein the coupling element comprises a seating arrangement for a nozzle of a bone cement applicator.

57. A method in accordance with claim 40, wherein a diameter of the screw body is greater than a pitch of the external thread.

58. A method in accordance with claim 40, wherein the external thread comprises a self-tapping external thread.

59. A system for stabilising bone elements, comprising:
a bone screw with external threads for securing adjacent bone elements together, said bone screw having a screw body with a hollow channel extending longitudinally therein;
a bone cement applicator for injecting bone cement into said hollow channel of said screw body; and
a coupling element adapted to couple said bone cement applicator to said bone screw;
wherein:
at least one longitudinal recess is formed on the periphery of the screw body which is connected to the hollow channel along at least a portion of a length of said hollow channel, said at least one longitudinal recess extending transversely relative to at least one of a radial direction and a peripheral direction, and said at least one longitudinal recess extending over a plurality of turns of the external thread in a longitudinal direction; and
said bone cement when injected is enabled to flow into said at least one longitudinal recess from said hollow channel and into intermediary spaces between said turns of the external thread to produce a cement jacket substantially around said screw body.

* * * * *